(12) United States Patent
Muller et al.

(10) Patent No.: US 7,901,906 B2
(45) Date of Patent: Mar. 8, 2011

(54) TARGETING OF MKRN1 FOR IDENTIFYING CANCER TREATMENT AGENTS

(75) Inventors: Mark T. Muller, Port Orange, FL (US); In Kwon Chung, Seoul (KR)

(73) Assignee: University of Central Florida Research Foundation, Inc., Orlando, FL (US)

( * ) Notice: Subject to any disclaimer, the term of this patent is extended or adjusted under 35 U.S.C. 154(b) by 236 days.

(21) Appl. No.: 11/279,151

(22) Filed: Apr. 10, 2006

(65) Prior Publication Data

US 2007/0224199 A1   Sep. 27, 2007

Related U.S. Application Data

(60) Provisional application No. 60/785,414, filed on Mar. 23, 2006.

(51) Int. Cl.
 *C12N 15/00* (2006.01)
(52) U.S. Cl. .............................. 435/69.1; 435/6; 435/7.1
(58) Field of Classification Search ................. 435/69.1, 435/6, 7.1
See application file for complete search history.

(56) References Cited

U.S. PATENT DOCUMENTS

| | | | | |
|---|---|---|---|---|
| 6,831,154 B1 * | 12/2004 | Bartel | ........................... | 530/350 |
| 2007/0105114 A1 * | 5/2007 | Li et al. | ............................. | 435/6 |

OTHER PUBLICATIONS

Kaiser (Science, 2006, 313, 1370).*
Gura, 1997, (Science, 278:1041-1042).*
Ezzell, 1995 (J. NIH Res, 7:46-49).*
Boon, 1992 (Adv Can Res, 58:177-210).*
Smith RT, 1994 (Clin Immunol, 41(4): 841-849).*
Bodey et al, 2000, Anticancer Res, 20: 2665-2676.*
Lee et al, 1999, J Immunol, 163: 6292-6300.*
Hsieh et al, 2007 (British J cancer, 97: 453-457).*
Bowie (Science, 1990, 257:1306-1310).*
Burgess et al ( J of Cell Bio. 111:2129-2138, 1990).*
Lazar et al (Molecular and Cellular Biology, 1988, 8:1247-1252).*
MPSRCH search result, 2008, us-11-279-151-12.rapbm, result 4, pp. 1-2.*
Kim et al, May 2005 (Genes and Development, 19(7): 776-81).*

* cited by examiner

*Primary Examiner* — Misook Yu
*Assistant Examiner* — Minh-Tam Davis
(74) *Attorney, Agent, or Firm* — Timothy H. Van Dyke; Beusse Wolter Sanks Mora & Maire

(57) ABSTRACT

Disclosed herein are novel methods for screening for compounds useful in treating telomerase positive cancers. In exemplary embodiments, screening methods are based on the implementation or manipulation of therapeutic agents that up-regulate activity or expression of MKRN polypeptides or polynucleotides encoding the same, respectively. The methods are useful in identifying agents that can serve as cancer therapeutic agents.

1 Claim, 5 Drawing Sheets

TARGETING OF MKRN1 FOR IDENTIFYING CANCER TREATMENT AGENTS

CROSS-REFERENCE TO RELATED APPLICATIONS

This application is related to U.S. Provisional application Ser. No. 60/785,414 filed Mar. 23, 2006, and claims priority to such application under 35 USC §119.

BACKGROUND

Telomeres are essential and functional components of the physical ends of eukaryotic chromosomes (Blackburn 1991; Greider 1996). Telomeres enable cells to distinguish chromosome ends from double-strand breaks in the genome. Without functional telomeres, the chromosomes are prone to nucleolytic degradation leading to cell death through apoptosis and may rearrange by genetic recombination or end-to-end fusion (Counter et al. 1992; Blasco et al. 1997; Artandi et al. 2002). Most normal human somatic cells show a progressive loss of telomeric DNA during successive rounds of cell division due to a DNA end replication problem (Lingner et al. 1995). Thus, telomere shortening has been proposed as a ticketing mechanism that controls the replicative capacity of cells and cellular senescence (Harley 1991). Cells with extended replicative life spans have mechanisms to counteract loss of telomeric DNA. In most human cancer cells, telomere shortening is alleviated by telomerase, a ribonucleoprotein enzyme that is composed of a catalytic subunit, hTERT, and its template RNA, hTR (Blackburn 1992; Counter et al. 1992). Telomerase activity is detectably expressed in the majority of human cancer cells but is repressed in most normal somatic cells (Kim et al. 1994). Since introduction of hTERT gene into normal somatic cells extends the life-span of the cells, the immortalized phenotype of most cancer cells would involve activation of telomerase (Bodnar et al. 1998).

Telomerase activity correlates with hTERT expression, implicating this catalytic subunit as the rate-limiting component of the telomerase holoenzyme (Nakamura and Cech 1998). Although telomerase activity is regulated by gene expression for hTERT (Wang et al. 1998; Wu et al. 1999; Meyerson et al. 1997), several lines of evidence have suggested a post-translational regulation of telomerase activity. One possible mechanism for the post-translational modification of telomerase is the interaction of hTERT with accessory proteins such as enzymes, chaperones, and polypeptide modifiers (Lee et al. 2004; Liu 1999; Zhou and Lu 2001). Recent studies have shown that the molecular chaperone Hsp90 binds specifically to hTERT to promote the assembly of active telomerase both in a cell-free system and in intact cells (Holt et al. 1999). Moreover, inhibition of Hsp90 function in cells blocks assembly of active telomerase. However, the underlying mechanism has not been elucidated.

Identifying cellular mechanisms that control the activity of telomerases may provide new and helpful targets for establishing new cancer therapy agents.

DETAILED DESCRIPTION

Figure 1:
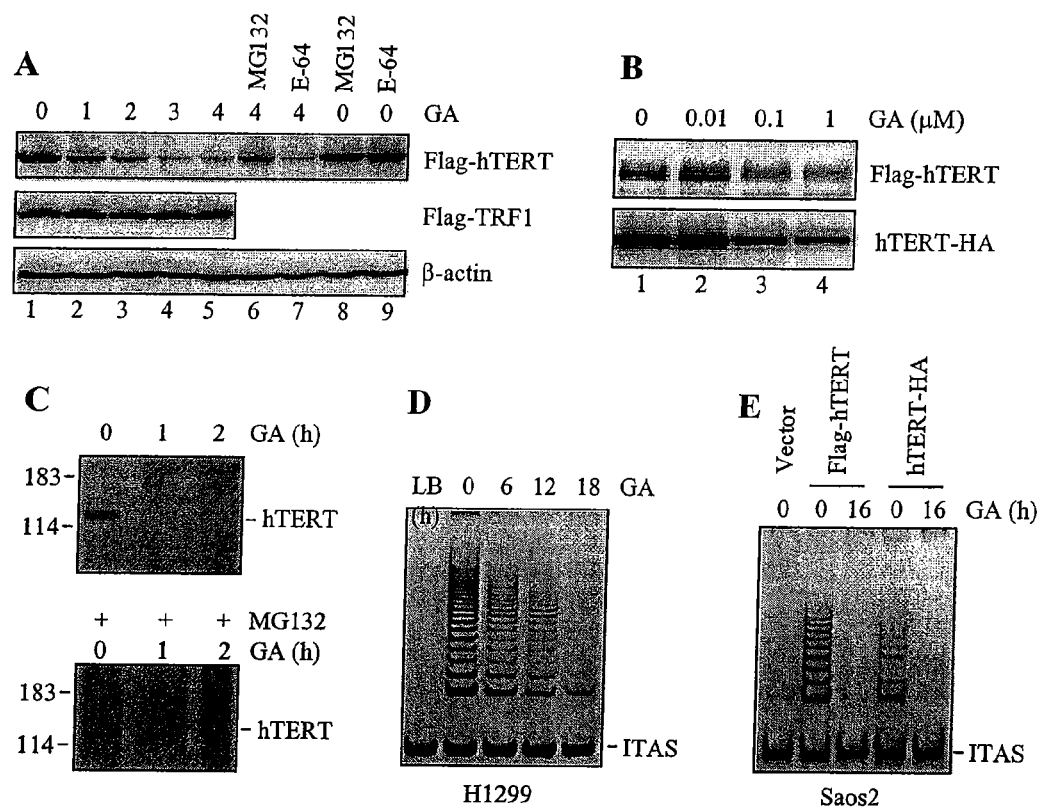
FIG. 1. hTERT is sensitive to the Hsp90 antagonist geldanamycin. (A) Down-regulation of ectopically expressed hTERT by GA. H1299 cells transfected with Flag-hTERT or Flag-TRF1 were treated with 0.1 µM GA for the indicated times. Lysates were resolved on 8% SDS-PAGE and analyzed by immunoblotting using an anti-Flag antibody probe. Cells were pretreated with 10 µM MG132 or E-64 for 2 hours, either alone or before treatment with GA. (B) Concentration dependence of GA on hTERT. H1299 cells transfected with Flag-hTERT or hTERT-HA were treated for 2 hours with the GA concentration indicated. The hTERT polypeptides were visualized with anti-Flag or anti-HA antibodies as marked by each blot. (C) Down-regulation of endogenous hTERT by GA. H1299 cells were treated with 0.1 µM GA for the indicated times, and cell lysates were analyzed by immunoprecipitation with anti-hTERT antibody followed by immunoblotting using same antibody probe. Cells were pretreated with 10 µM MG132 for 2 hours, either alone or before treatment with GA. Molecular weight markers are shown in kilodaltons. (D) H1299 cells were treated with 0.1 µM GA for the indicated times, and cell lysates were analyzed for telomerase activity by the TRAP assay. The lane labeled LB corresponds to the negative control (lysis buffer only). ITAS represents the internal telomerase assay standard. (E) Saos-2 cells transfected with Flag-hTERT or hTERT-HA or empty vector were untreated or treated with 0.1 µM GA for 16 hours, and cell lysates were analyzed for telomerase activity using the TRAP assay.

The subject invention is based on the inventors discovery that ubiquitination of telomerase is induced by a novel protein MKRN-1. The up-regulation of MKRN-1 induces ubiquitination of one or more components of telomerase which causes a degradation in telomerase activity. The degradation of telomerase activity ultimately leads to degradation of telomeres in the cells, and eventually cell death. Cells of many types of cancers are known to be telomerase positive. Thus, the inventors discovery enables the targeting of MKRN-1 to serve as a basis for novel cancer therapies.

Not being bound by any particular theory, the inventors found that disruption of Hsp90 function by geldanamycin (GA) promotes ubiquitination and proteasome-mediated degradation of hTERT. Furthermore, they have identified a novel hTERT binding protein MKRN1 that functions as an E3 ligase and mediates ubiquitination of hTERT in vivo and in vitro. Overexpression of MKRN1 in telomerase-positive cells decreases telomerase activity and telomere length. These observations indicate that MKRN1, a post-translational modifier of hTERT, exerts a negative role in telomere length homeostasis.

A particular embodiment of the subject invention pertains to methods of screening for test compounds that modulate the activity of MKRN-1 polypeptides. Another embodiment of the subject invention pertains to therapeutic agents that up-regulate MKRN-1 activity. A further embodiment of the subject invention pertains to methods of treating cancers by administrating therapeutic agents that up-regulate MKRN-1 activity.

In reviewing the detailed disclosure which follows, and the specification more generally, it should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

1. Screening Methods

The invention provides assays for screening test compounds which bind to or modulate the activity of an MKRN polypeptide or bind to and inhibit or affect expression of an MKRN polynucleotide. A test compound preferably binds to an MKRN polypeptide. More preferably, a test compound decreases or increases MKRN activity by at least about 10, preferably about 50, more preferably about 75, 90, or 100% relative to the absence of the test compound.

1.1. Test Compounds

Test compounds relate to agents that potentially have therapeutic activity, i.e., bind to or modulate the activity of an MKRN polypeptide or bind to or affect expression of an MKRN polynucleotide. Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. NatL. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994;

Carell et al., Angew. Chem. Int. Ed. Engl. 33, 2061; Gallop et al., J. Med. Chem. 37, 1233, 1994).

1.2. High Throughput Screening

Test compounds can be screened for the ability to bind to and up-regulate MKRN polypeptides or polynucleotides or to affect MKRN activity or MKRN gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format. Alternatively, "free format assays," or assays that have no physical barrier between samples, can be used.

1.3. Binding Assays

For binding assays, the test compound is preferably, but not necessarily, a small molecule which binds to and occupies, for example, the active site of the MKRN polypeptide, such that normal biological activity is prevented. Examples of such small molecules include, but are not limited to, small peptides or peptide-like molecules, or non-peptide small molecules such as organics identified by high throughput screens (e.g., chemical library screening).

In binding assays, either the test compound or the MKRN polypeptide can comprise a detectable label, such as a fluorescent, radioisotopic, chemiluminescent, or enzymatic label, such as horseradish peroxidase, alkaline phosphatase, or luciferase. Detection of a test compound which is bound to the MKRN polypeptide can then be accomplished, for example, by direct counting of radioemmission, by scintillation counting, or by determining conversion of an appropriate substrate to a detectable product.

Those skilled in the art equipped with teachings herein will appreciate that there are multiple conventional methods of detecting binding of a test compound. For example, binding of a test compound to a MKRN polypeptide can be determined without labeling either of the interactants. A microphysiometer can be used to detect binding of a test compound with an MKRN polypeptide. A microphysiometer (e.g., CYTOSENSOR™) is an analytical instrument that measures the rate at which a cell acidifies its environment using a light-addressable potentiometric sensor (LAPS). Changes in this acidification rate can be used as an indicator of the interaction between a test compound and an MKRN polypeptide (McConnell et al., Science 257, 19061912, 1992).

In another alternative example, determining the ability of a test compound to bind to an MKRN polypeptide can be accomplished using a technology such as real-time Bimolecular Interaction Analysis (BIA) (Sjolander & Urbaniczky, Anal Chem. 63, 23382345, 1991, and Szabo et al., Curr. Opin. Struct. Biol. 5, 699705, 1995). BIA is a technology for studying biospecific interactions in real time, without labeling any of the interactants (e.g., BIAcore.™). Changes in the optical phenomenon surface plasmon resonance (SPR) can be used as an indication of real-time reactions between biological molecules.

In yet another aspect of the invention, an MKRN polypeptide can be used as a "bait protein" in a two-hybrid assay or three-hybrid assay (see, e.g., U.S. Pat. No. 5,283,317; Zervos et al., Cell 72, 223232, 1993; Madura et al., J. Biol. Chem. 268, 1204612054, 1993; Bartel et al., BioTechniques 14, 920924, 1993; Iwabuchi et al., Oncogene 8, 16931696, 1993; and Brent WO94/10300), to identify other proteins which bind to or interact with the MKRN polypeptide and modulate its activity.

In many screening embodiments, it may be desirable to immobilize either the MKRN polypeptide (or polynucleotide) or the test compound to facilitate separation of bound from unbound forms of one or both of the interactants, as well as to accommodate automation of the assay. Thus, either the MKRN polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the MKRN polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a MKRN polypeptide (or polynucleotide) can be accomplished in any vessel suitable for containing the reactants. Examples of such vessels include microtiter plates, test tubes, and microcentrifuge tubes.

In a specific embodiment, the MKRN polypeptide may be a fusion protein comprising a domain that allows the MKRN polypeptide to be bound to a solid support. For example, glutathione S-transferase fusion proteins can be adsorbed onto glutathione sepharose beads (Sigma Chemical, St. Louis, Mo.) or glutathione derivatized microtiter plates, which are then combined with the test compound or the test compound and the nonadsorbed MKRN polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a MKRN polypeptide (or polynucleotide) or a test compound can be immobilized utilizing conjugation of biotin and streptavidin. Biotinylated MKRN polypeptides (or polynucleotides) or test compounds can be prepared from biotinNHS(Nhydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a MKRN polypeptide, polynucleotide, or a test compound, but which do not interfere with a desired binding site, such as the active site of the MKRN polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the MKRN polypeptide or test compound, enzyme-linked assays which rely on detecting an activity of the MKRN polypeptide, and SDS gel electrophoresis under non-reducing conditions.

Screening for test compounds which bind to a MKRN polypeptide or polynucleotide also can be carried out in an intact cell. Any cell which comprises a MKRN polypeptide or polynucleotide can be used in a cell-based assay system. A MKRN polynucleotide can be naturally occurring in the cell or can be introduced using techniques such as those described above. Binding of the test compound to a MKRN polypeptide or polynucleotide is determined as described above.

1.4. Enzyme Assays

Test compounds can be tested for the ability to increase or decrease the MKRN activity of a MKRN polypeptide. MKRN activity can be measured, for example, by adapting techniques such as that described in U.S. Pat. No. 4,529,693 (see Example 2). Enzyme assays can be carried out after contacting either a purified MKRN polypeptide, a cell membrane preparation, or an intact cell with a test compound. A test compound which decreases ligase activity of a MKRN polypeptide by at least about 10, preferably about 50, more preferably about 75, 90, or 100% is identified as a potential therapeutic agent for decreasing MKRN activity. A test compound which increases ligase MKRN polypeptide by at least about 10, preferably about 50, more preferably about 75, 90, or 100% is identified as a potential therapeutic agent for increasing MKRN activity.

1.5. Gene Expression

In another embodiment, test compounds which increase or decrease MKRN gene expression are identified. An MKRN polynucleotide is contacted with a test compound, and the expression of an RNA or polypeptide product of the MKRN polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of MKRN mRNA or polypeptide expression in the cells can be determined by methods well known in the art for detecting mRNA or polypeptide. Either qualitative or quantitative methods can be used. The presence of polypeptide products of an MKRN polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a MKRN polypeptide.

Such screening can be carried out either in a cell-free assay system or in an intact cell. Any cell which expresses a MKRN polynucleotide can be used in a cell-based assay system. The MKRN polynucleotide can be naturally occurring in the cell or can be introduced using techniques such as those described above. Either a primary culture or an established cell line, such as CHO or human embryonic kidney 293 cells, can be used.

2. Pharmaceutical Compositions

The invention also pertains to pharmaceutical compositions comprising one or more therapeutic agents that are identified by screening methods that utilize MKRN polypeptides and/or polynucleotides. Therapeutic agent(s) can be administered to a patient to achieve a therapeutic effect, i.e. useful cancer therapy. Pharmaceutical compositions of the invention can comprise, for example, therapeutic agents identified by a screening method embodiment described herein, which are identified by their ability to bind to or affect activity of MKRN polypeptides, or bind to and/or affect expression MKRN polynucleotides. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

This invention further pertains to the use of novel agents identified by the screening assays described above. Accordingly, it is within the scope of this invention to use a therapeutic agent identified as described herein in an appropriate animal model. For example, an agent identified as described herein (for example, but not limited to., a modulating agent, an antisense nucleic acid molecule, a specific antibody, ribozyme, or a MKRN polypeptide binding molecule) can be used in an animal model to determine the efficacy, toxicity, or side effects of treatment with such an agent. Furthermore, this invention pertains to uses of novel agents identified by the above described screening assays for treatments as described herein.

Those skilled in the art will appreciate that numerous delivery mechanisms are available for delivering a therapeutic agent to an area of need. By way of example, the agent may be delivered using a liposome as the delivery vehicle. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmole of liposome delivered to about $10^6$ cells, and even more preferably about 2.0 µg of DNA per 16 nmol of liposome delivered to about 10⁶ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202-05 (1993); Chiou et al., GENE THERAPEUTICS: METHODS AND APPLICATIONS OF DIRECT GENE TRANSFER (J. A. Wolff, ed.) (1994); Wu & Wu, J. Biol. Chem. 263, 621-24 (1988); Wu et al., J. Biol. Chem. 269, 542-46 (1994); Zenke et al., Proc. Natl. Acad. Sci. U.S.A. 87, 3655-59 (1990); Wu et al., J. Biol. Chem. 266, 338-42 (1991).

2.1 Determination of a Therapeutically Effective Dose

The determination of a therapeutically effective dose of therapeutic agents identified by a screening method herein is well within the capability of those skilled in the art. A therapeutically effective dose refers to that amount of active ingredient which attenuates or eliminates TB infection contrasted to TB infection or attenuation that occurs in the absence of the therapeutically effective dose.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Preferably, a therapeutic agent reduces expression of an MKRN gene or the activity of an MKRN polypeptide by at least about 10, preferably about 50, more preferably about 75, 90, or 100% relative to the absence of the reagent. The effectiveness of the mechanism chosen to decrease the level of expression of an MKRN gene or the activity of an MKRN polypeptide can be assessed using methods well known in the art, such as hybridization of nucleotide probes to MKRN-specific mRNA, quantitative RT-PCR, immunologic detection of an MKRN polypeptide, or measurement of MKRN activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy.

3. Polypeptides

MKRN polypeptides according to the invention comprise at least 12, 15, 25, 50, 75, 100, 125, 150, 175, 200, 225, 250 or 265 contiguous amino acids selected from the amino acid sequence shown in SEQ ID NO: 2, or a biologically active variant thereof, as defined below. A MKRN polypeptide of the invention therefore can be a portion of an MKRN protein, a full-length MKRN protein, or a fusion protein comprising all or a portion of MKRN protein.

3.1 Biologically Active Variants

MKRN polypeptide variants which are biologically active, i.e., confer an ability to initiate degradation of hTERT, also are considered MKRN polypeptides for purposes of this application. Preferably, naturally or non-naturally occurring MKRN polypeptide variants have amino acid sequences which are at least about 55, 60, 65, or 70, preferably about 75, 80, 85, 90, 96, 96, or 98% identical to the amino acid sequence shown in SEQ ID NO: 2 or a fragment thereof. Percent identity between a putative MKRN polypeptide variant and an amino acid sequence of SEQ ID NO: 2 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an MKRN polypeptide can be found using computer programs well known in the art, such as DNASTAR software. Whether an amino acid change results in a biologically active MKRN polypeptide can readily be determined by assaying for MKRN activity, as described for example, in the specific Examples, below.

3.2 Fusion Proteins

In some embodiments of the invention, it is useful to create fusion proteins. By way of example, fusion proteins are useful for generating antibodies against MKRN polypeptide amino acid sequences and for use in various assay systems. For example, fusion proteins can be used to identify proteins which interact with portions of an MKRN polypeptide. Protein affinity chromatography or library-based assays for protein-protein interactions, such as the yeast two-hybrid or phage display systems, can be used for this purpose. Such methods are well known in the art and also can be used as drug screens.

A MKRN polypeptide fusion protein comprises two polypeptide segments fused together by means of a peptide bond. For example, the first polypeptide segment can comprise at least 12, 15, 25, 50, 75, 100, 125, 150, 175, 200, 225, or 250 contiguous amino acids of SEQ ID NO: 2 or of a biologically active variant, such as those described above. The first polypeptide segment also can comprise full-length MKRN protein.

The second polypeptide segment can be a full-length protein or a protein fragment. Proteins commonly used in fusion protein construction include galactosidase, glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the MKRN polypeptide-encoding sequence and the heterologous protein sequence, so that the MKRN polypeptide can be cleaved and purified away from the heterologous moiety.

Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

3.3 Obtaining Polypeptides

MKRN polypeptides can be obtained, for example, by purification of polypeptides from cells, expressing MKRN polynucleotide(s) and other appropriate methods as will be appreciated by those skilled in the art in view of the teachings herein.

3.4 Protein Purification

MKRN polypeptides can be purified from any cell which expresses the enzyme, including host cells which have been transfected with MKRN enzyme expression constructs. A purified MKRN enzyme polypeptide is separated from other compounds which normally associate with the MKRN enzyme polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified MKRN polypeptides is at least 80% pure; preferably, the preparations are 90%, 95%, or 99% pure. Purity of the preparations can be assessed by any means known in the art, such as SDS-polyacrylamide gel electrophoresis.

4. Polynucleotides

An MKRN polynucleotide can be single- or double-stranded and comprises a coding sequence or the complement of a coding sequence for an MKRN polypeptide. A coding sequence for MKRN polypeptide of SEQ ID NO: 2 is shown in SEQ ID NO: 1.

Degenerate nucleotide sequences encoding MKRN polypeptides, as well as homologous nucleotide sequences which are at least about 50, 55, 60, 65, 60, preferably about 75, 90, 96, or 98% identical to the nucleotide sequence shown in SEQ ID NO: 1 also are MKRN polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of MKRN polynucleotides which encode biologically active MKRN polypeptides also are MKRN polynucleotides.

4.1 Identification of Polynucleotide Variants and Homologs

Variants and homologs of the MKRN polynucleotides described above also are MKRN polynucleotides. Typically, homologous MKRN polynucleotide sequences can be identified by hybridization of candidate polynucleotides to known MKRN polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of the MKRN polynucleotides disclosed herein also can be identified by making suitable probes or primers and screening cDNA expression libraries. It is well known that the Tm of a double-stranded DNA decreases by 1-1.5° C. with every 1% decrease in homology (Bonner et al., J. Mol. Biol. 81, 123 (1973). Variants of MKRN polynucleotides or polynucleotides of other species can therefore be identified by hybridizing a putative homologous MKRN polynucleotide with a polynucleotide having a nucleotide sequence of SEQ ID NO: 1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to MKRN polynucleotides or their complements following stringent hybridization and/or wash conditions also are MKRN polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between an MKRN polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m = 81.5°\text{C.} - 16.6(\log_{10}[\text{Na}^+]) + 0.41(\% \, G+C) - 0.63(\% \, \text{formamide}) - 600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

4.2 Preparation of Polynucleotides

A naturally occurring MKRN polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated MKRN polynucleotides. For example, restriction enzymes and probes can be used to isolate polynucleotide fragments which comprises MKRN nucleotide sequences. Isolated polynucleotides are in preparations which are free or at least 70, 80, or 90% free of other molecules.

MKRN DNA molecules can be made with standard molecular biology techniques, using MKRN mRNA as a template. MKRN DNA molecules can thereafter be replicated using molecular biology techniques known in the art and disclosed in manuals such as Sambrook et al. (1989). An amplification technique, such as PCR, can be used to obtain additional copies of polynucleotides of the invention. The inventors have successfully demonstrated this approach.

Alternatively, synthetic chemistry techniques can be used to synthesizes MKRN polynucleotides. The degeneracy of the genetic code allows alternate nucleotide sequences to be synthesized which will encode a MKRN polypeptide having, for example, an amino acid sequence shown in SEQ ID NO: 2 or a biologically active variant thereof.

4.3 Expression of Polynucleotides

To express a MKRN polynucleotide, the polynucleotide can be inserted into an expression vector which contains the necessary elements for the transcription and translation of the inserted coding sequence. Methods which are well known to those skilled in the art can be used to construct expression vectors containing sequences encoding MKRN polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a MKRN enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those nontranslated regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an MKRN polypeptide, vectors based on SV40 or EBV can be used with an appropriate selectable marker.

5. Host Cells

According to certain embodiments of the subject invention, an MKRN polynucleotide will need to be inserted into a host cell, for expression, processing and/or screening. A host cell strain can be chosen for its ability to modulate the expression of the inserted sequences or to process the expressed MKRN polypeptide in the desired fashion. Such modifications of the polypeptide include, but are not limited to, acetylation, carboxylation, glycosylation, phosphorylation, lipidation, and acylation. Posttranslational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high yield production of recombinant proteins. For example, cell lines which stably express MKRN polypeptides can be transformed using expression vectors which can contain viral origins of replication and/or endogenous expression elements and a selectable marker gene on the same or on a separate vector. Following the introduction of the vector, cells can be allowed to grow for 12 days in an enriched medium before they are switched to a selective medium. The purpose of the selectable marker is to confer resistance to selection, and its presence allows growth and recovery of cells which successfully express the introduced MKRN sequences. Resistant clones of stably transformed cells can be proliferated using tissue culture techniques appropriate to the cell type. See, for example, ANIMAL CELL CULTURE, R. I. Freshney, ed., 1986.

5.1 Detecting Expression

A variety of protocols for detecting and measuring the expression of a MKRN polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a MKRN polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., J. Exp. Med. 158, 12111216, 1983).

5.2 Expression and Purification of Polypeptides

Host cells transformed with nucleotide sequences encoding MKRN polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode MKRN polypeptides can be designed to contain signal sequences which direct secretion of soluble MKRN polypeptides through a prokaryotic or eukaryotic cell membrane or which direct the membrane insertion of membrane-bound MKRN polypeptide.

6. Antibodies

Antibodies are referenced herein and various aspects of the subject invention utilize antibodies specific to MKRN polypeptide(s). As described above, one example of an therapeutic agent may pertain to an antibody. Any type of antibody known in the art can be generated to bind specifically to an epitope of an MKRN polypeptide. "Antibody" as used herein includes intact immunoglobulin molecules, as well as fragments thereof, such as Fab, F(ab')$_2$, and Fv, which are capable of binding an epitope of an MKRN polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an MKRN polypeptide can be used therapeutically, as mentioned, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. Antibodies useful for embodiments of the subject invention may be polyclonal, but are preferably monoclonal antibodies.

7. Identification of Differentially Expressed Genes and Profiling of Cancers

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987-1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., Proc. Natl. Acad. Sci. U.S.A. 85, 208-12, 1988), subtractive hybridization (Hedrick et al., Nature 308, 149-53; Lee et al., Proc. Natl. Acad. Sci. U.S.A. 88, 2825, 1984), and differential display (Liang & Pardee, Science 257, 967-71, 1992; U.S. Pat. No. 5,262,311), and microarrays.

The differential expression information may itself suggest relevant methods for the treatment of disorders involving degradation of telomeres. For example, treatment may include a modulation of expression of the differentially expressed genes and/or the gene encoding the MKRN polypeptides. The differential expression information may indicate whether the expression or activity of the differentially expressed gene or gene product or the MKRN gene or gene product are up-regulated or down-regulated.

Further, use of anti-MKRN antibodies can be used to screen for tumors possessing varying expression of MKRN polypeptides. As the characterization of tumors possessing MKRN expression is elucidated, this information will be useful in determining metastatic potential of a given tumor, which in turn will assist in determining an appropriate treatment regime. Also, related to the foregoing, as drugs are developed and identified that affect MKRN activity and/or expression, screening of tumors will facilitate selection of appropriate anti-cancer agents. Accordingly, another embodiment of the invention pertains to a method of screening of a tumor cell for MKRN expression.

Example 1

Cell Lines and Culture Conditions

The human lung carcinoma cell line H1299 was cultured in RPMI-1640 medium, and the human fibrosarcoma cell line HT1080 was cultured in Dulbecco's modified Eagle's medium supplemented with 10% fetal bovine serum, 100 units/ml penicillin, and 100 µg/ml streptomycin in 5% $CO_2$ at 37° C. The human osteosarcoma cell line Saos-2 was maintained in McCoy's 5A medium containing 15% fetal bovine serum, 100 units/ml penicillin, and 100 µg/ml streptomycin. To establish cell lines stably expressing MKRN1, the MKRN1-V5 construct was transfected into HT1080 cells using Lipofectamine Plus (Invitrogen, Carlsbad, Calif.) according to the manufacturer's instructions. As a control, HT1080 cells were also stably transfected with an empty vector. Multiple independent single clones were isolated and checked for protein expression by immunoblotting with anti-V5 antibody.

Expression Vectors

The Flag-hTERT expression vector was constructed by cloning the full-length hTERT cDNA into pCMV-Tag2 vector (Stratagene). The hTERT-HA expression vector (generously provided by H. Seimiya, Japanese Foundation for Cancer Research) has been described (Seimiya et al. 2000). The MKRN1 expression vector was constructed by inserting the EcoRI and NotI fragment from the full-length MKRN1 cDNA (generated by PCR with the appropriate synthetic primers) into pcDNA3.1 (Invitrogen, Carlsbad, Calif.). The expression vector for GST-hTERT-HA was constructed by cloning the fragment encoding the C-terminal region (amino acid 946-1132) of hTERT into pGEX-5X-2 (Amersham Biosciences Inc., Piscataway, N.J.). MKRN1 and MKRN1 mutants were subcloned into pGEX-6P-1 for expression in bacteria. The GST fusion proteins were expressed, purified, and cleaved with PreScission™ protease to remove the cleaved GST according to the manufacturer's instructions (Amersham Biosciences Inc., Piscataway, N.J.).

Yeast Two-Hybrid Screening

Yeast two-hybrid screening was performed as described (Lee et al. 2004). Briefly, the yeast strain EGY48 harboring pLexA-hTERT (amino acid 946-1132) and pSH18-34 was transformed by the lithium acetate method with a HeLa cDNA library fused to the activation domain vector pB42AD (Clontech).

Immunoprecipitation and Immunoblotting

H1299 cells were transiently transfected with the expression vectors indicated in the figure legends using TransFast transfection reagent (Promega, Madison, Wis.) according to the manufacturer's instructions. Cells were lysed with buffer containing 0.5% NP-40, 50 mM Tris-HCl (pH 7.5), 150 mM NaCl, 2 mM phenyl methylsulphonyl fluoride. After centrifugation at 12,000 rpm for 30 min, the supernatants were immunoprecipitated for 2 hours with anti-Flag (Sigma, St. Louis, Mo.) or anti-HA (Santa Cruz biotechnology, Santa Cruz, Calif.) antibodies and then incubated with Sepharose beads conjugated to Protein G (Amersham Biosciences Inc., Piscataway, N.J.). When ubiquitin conjugates of hTERT were detected, immunoprecipitation was performed with lysis buffer containing 0.1% SDS to dissociate its interacting proteins. Immunoblot analyses were performed using anti-hTERT (Santa Cruz biotechnology, Santa Cruz, Calif.), anti-V5 (Invitrogen, Carlsbad, Calif.), anti-HA, and anti-Flag antibodies.

In Vitro Ubiquitination Assay

GST-hTERT-HA expressed in bacteria was used as substrate for in vitro ubiquitination assay (Park et al. 2004). The ubiquitination reactions were carried out in buffer (50 mM Tris-HCl, pH 7.5, 2 mM ATP, 2.5 mM $MgCl_2$, 5 mM dithiothreitol, and 0.05% NP-40) containing yeast E1 (0.05 µg), E2 (0.2 µg), and $His_6$-ubiquitin (0.8 µg) (6×His disclosed as SEQ ID NO: 7) in a final volume of 30 µl. Purified wild-type or mutant MKRN1 as an E3 enzyme was added as indicated in the figure legend. The reaction mixtures were incubated at 30° C. for 60 min and terminated with sample loading buffer and run on SDS-PAGE. Slow migrating ubiquitin conjugates were visualized by immunoblot analysis with anti-HA antibody.

Telomerase Assays

The telomeric repeat amplification protocol (TRAP) was used as previously described (Kim et al. 2003). Cell extracts (200 ng of protein) were added to telomerase extension reactions and incubated for 20 min at 37° C. Reactions were stopped by heating at 94° C. for 90 seconds and placed on ice. PCR was performed using the TS primer and ACX primer for 30 cycles (denaturation at 94° C. for 30 s, annealing at 60° C. for 30 s, and extension at 72° C. for 30 s). As an internal telomerase assay standard (ITAS), NT and TSNT primers were added to the PCR mixture as previously described (Kim and Wu 1997). Telomerase products were resolved by electrophoresis on a 12% nondenaturing polyacrylamide gel. Bands were then visualized by staining with SYBR Green (Molecular Probes, Eugene, Oreg.). The signal intensity was quantified with a LAS-1000 Plus Image analyzer (Fuji Photo Film, Tokyo, Japan).

Terminal Restriction Fragment (TRF) Analysis

To measure the telomere length, genomic DNA was digested with RsaI and HinfI and separated on 0.7% agarose gel. DNA samples were transferred to a nylon membrane (Hybond N+, Amersham Biosciences Inc., Piscataway, N.J.) and hybridized with a $^{32}P$ labeled probe $(TTAGGG)_{20}$ (SEQ ID NO: 6). Signals were detected by phosphoimage analyzer (Fuji Photo Film, Tokyo, Japan).

hTERT is Sensitive to the Hsp90 Antagonist Geldanamycin

Inhibition of Hsp90 function by GA prevents the assembly of active telomerase (Holt et al. 1999). Because GA mediates the dissociation of Hsp90 from its client proteins and promotes rapid degradation by the proteasome (Goetz et al. 2003), the inventors believed that hTERT would be sensitive to the Hsp90 antagonist. To investigate this possibility, the inventors transfected H1299 cells with Flag-tagged hTERT and assessed protein levels in the absence or presence of GA. hTERT protein was highly expressed in untreated cells but was down-regulated in a time-dependent manner in response to GA treatment, with over 50% of the protein being eliminated within 2 hours of treatment (FIG. 1A, lanes 1-5). TRF1 expression levels were not affected by GA treatment (FIG. 1A, middle blot). GA also decreased the level of hTERT expression in a dose-dependent manner (FIG. 1B). To verify the ability of GA to down-regulate endogenous hTERT levels, H1299 cells were treated with GA and immunoblotted using a polyclonal anti-hTERT antibody. Treatment of cells with GA significantly decreased endogenous hTERT levels (FIG. 1C, upper blot).

The Hsp90 chaperone complex binds to hTERT and influences proper assembly with hTR to form an active enzyme (Holt et al. 1999; Forsythe et al. 2001). The inventors tested the influence of GA-induced degradation of hTERT on telomerase activity in H1299 cells. Incubation with GA reduced telomerase activity in a time-dependent manner (FIG. 1D). To more clearly determine the effects of GA on telomerase activity, N-terminal Flag-tagged hTERT and C-terminal HA-tagged hTERT constructs were transfected to Saos-2 cells that lack detectable telomerase activity (Kim et al. 2003). The forced expression of exogenous hTERT produced telomerase activity in these cells (FIG. 1E). Furthermore, incubation with GA reduced telomerase activity to near basal levels. These results suggest that Hsp90 is not only important for the proper conformation of hTERT but also for maintaining telomerase assembly.

hTERT is Ubiquitinated and Degraded Via the Proteasomal Pathway

Reduction in hTERT levels could be due to degradation and/or turnover of the protein. To examine whether the GA-mediated degradation of hTERT proceeds via the proteasome, the inventors pretreated H1299 cells for 2 hours with the specific proteasome inhibitor, MG132, and subsequently incubated with GA for 4 hours. Incubation of cells with MG132 rescued the GA-induced down-regulation of hTERT (FIG. 1A, lane 6 in upper blot) whereas pretreatment of cells with the lysosomal proteolysis inhibitor E-64 had no effect on hTERT levels (compare lanes 6 and 7). In the absence of GA treatment, incubation of cells with either MG132 or E-64 alone did not cause a significant change in the levels of hTERT expression relative to untreated controls (FIG. 1A, lanes 8 and 9 in upper blot). These results indicate that GA-induced down-regulation of hTERT is due to degradation mediated by the proteasome pathway. The inventors also demonstrate that endogenous hTERT levels are affected by the proteasome pathway. Pretreatment of cells with MG132 before treatment with GA rescued the proteasomal degradation of the endogenous hTERT protein (FIG. 1C, lower blot).

Figure 2:
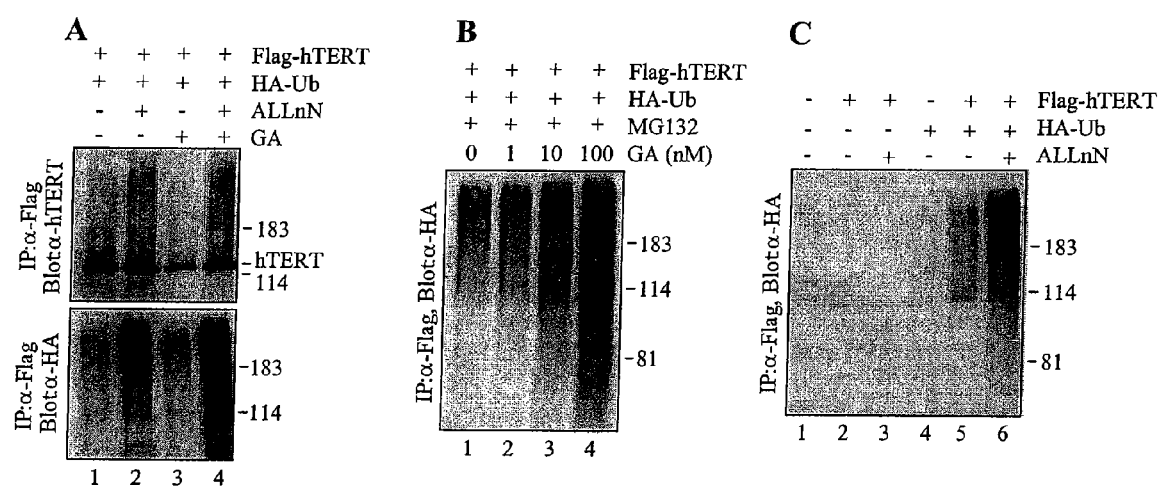
FIG. 2. hTERT is ubiquitinated prior to proteasome-mediated degradation. (A) H1299 cells were co-transfected with Flag-hTERT and HA-ubiquitin. Cells were either untreated or treated for 2 hours with 10 µg/ml ALLnN or 0.1 µM GA, or a combination of the two as specified above each lane. Immunoprecipitation was performed with anti-Flag antibody before probing with anti-hTERT or anti-HA antibodies as indicated besides each blot. Molecular weight markers are shown in kilodaltons. (B) H1299 cells co-transfected with Flag-hTERT and HA-ubiquitin were treated for 1 hour with the GA concentration indicated in the presence of 10 µM MG132. Immunoprecipitation was performed with anti-Flag antibody followed by immunoblotting using an anti-HA antibody probe. (C) H1299 cells co-transfected with Flag-hTERT and HA-ubiquitin were either untreated or treated for 2 hours with 10 µg/ml ALLnN as specified above each lane. Proteins were immunoprecipated with anti-Flag antibody followed by immunoblotting using an anti-HA antibody probe.

GA-mediated protein degradation by the proteasome depends on conjugation of ubiquitin to the Hsp90 client protein (Isaacs et al. 2002; Citri et al. 2002). To determine whether hTERT is ubiquitinated in vivo prior to its degradation, H1299 cells co-transfected with Flag-tagged hTERT and HA-tagged ubiquitin constructs were treated with GA, ALLnN (a general proteasome inhibitor) or both. The immunoprecipitated products were evaluated by immunoblotting with selected probes as described in FIG. 2. Treatment of GA alone decreased hTERT levels; however, GA plus ALLnN reversed this trend (FIG. 2A, compare lanes 3 and 4 in upper blot). Treatment with ALLnN alone did not affect hTERT levels relative to controls (FIG. 2A, compare lanes 1 and 2 in upper blot). Note that the amount of high molecular weight smearing was more noticeable in the ALLnN-treated cells (FIG. 2A, compare lanes 1 and 3 with lanes 2 and 4 in upper blot). To confirm that these slower migrating bands represented ubiquitinated hTERT, anti-Flag immunoprecipitates were probed with anti-HA antibody, which will illuminate ubiquitin-modified hTERT (FIG. 2A, lower blot). Again, ubiquitinated hTERT was dramatically elevated in the presence of the proteasome inhibitor ALLnN (FIG. 2A, compare lanes 1 and 3 with lanes 2 and 4 in lower blot). These high molecular smears are diagnostic for polyubiquitinated proteins (Girnta et al. 2003). This modification was substantially enhanced by the treating cells with both ALLnN and GA (FIG. 2A, compare lanes 2 and 4 in lower blot). In addition, hTERT displayed enhanced GA-induced ubiquitination in a dose-dependent manner in the presence of MG132 (FIG. 2B). These data indicate that hTERT is ubiquitinated in GA-treated cells prior to proteasome-dependent degradation in a manner similar to other Hsp90 client proteins (Isaacs et al. 2002; Citri et al. 2002). Without being bound to any particular theory, it is the inventors belief that two counteracting processes mediate hTERT levels: proteasomal degradation by the ubiquitination pathway and rescue (or protection) from degradation by Hsp90. The dynamic balance between these two processes determines equilibrium levels of hTERT, which then sets cellular telomerase activity. It is also worth noting that polyubiquitinated hTERT forms were significantly elevated by ALLnN even in the absence of GA treatment (FIG. 2C, lanes 5 and 6). These results suggest that hTERT is subject to ubiquitination even in the absence of GA.

Identification of a RING Finger Protein that Interacts with hTERT

Figure 3:
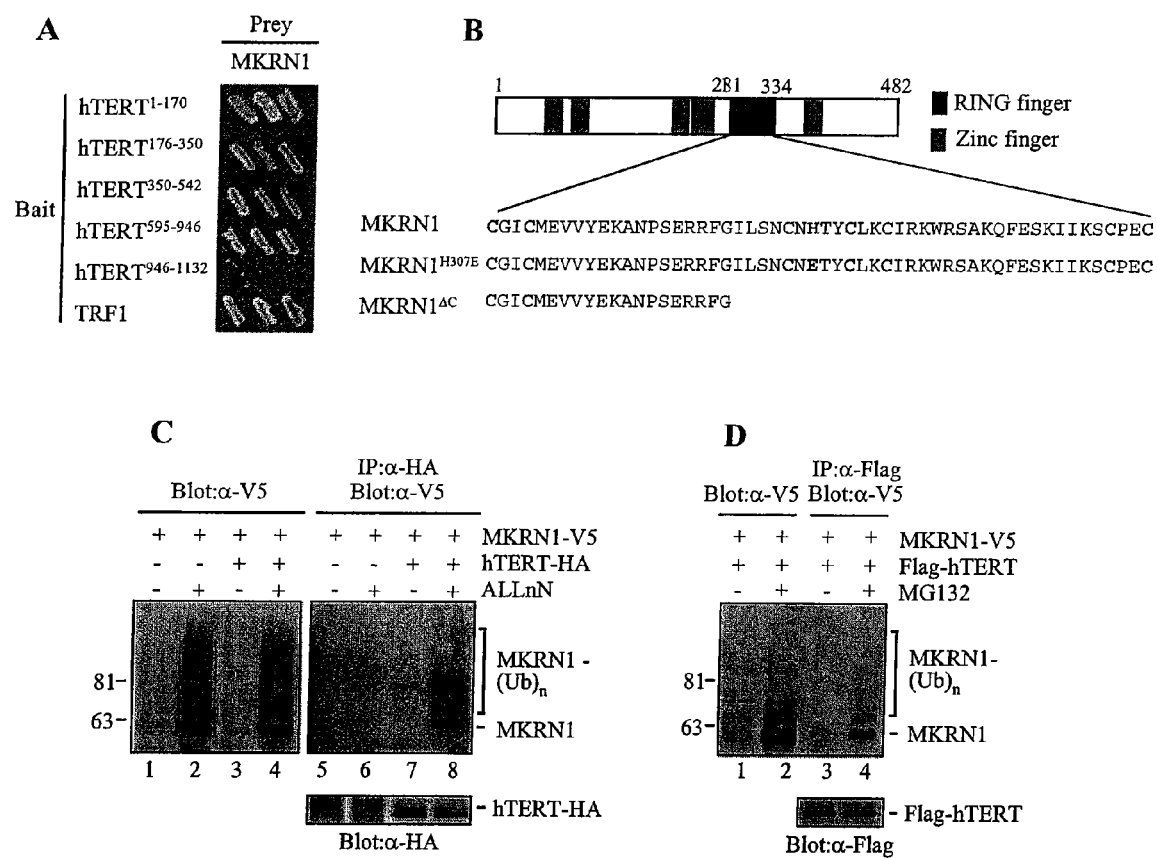
FIG. 3. MKRN1 interacts with hTERT. (A) Analysis of the physical interaction between hTERT and MKRN1 using the yeast two-hybrid assay. Five domains of hTERT were analyzed for binding to MKRN1. TRF1 bait was used as a negative control. Blue signal on the SG-HWU/X plate indicates activation of the reporter gene, LacZ. S, synthetic; G, galactose; H, histidine (−); W, tryptophan (−); U, uracil (−); X, X-gal. (B) Schematic diagram of MKRN1 domains. Amino acid sequences (SEQ ID NOS 3-5, respectively in order of appearance) surrounding the RING finger domain in MKRN1 and mutants used in this study. Cysteines and a histidine in the RING finger domain are shown in red. Mutated residue in MKRN1$^{H307E}$ is shown in blue. (C) H1299 cells co-transfected with hTERT-HA and MKRN1-V5 were either untreated or treated for 2 hours with 10 µg/ml ALLnN. Anti-HA immunoprecipitates were analyzed by immunoblotting using an anti-V5 antibody probe. The left panel shows the immunoblot of cell lysates (3% of the precipitated lysates) probed with anti-V5 antibody. hTERT-HA was visualized with an anti-HA antibody probe. (D) H1299 cells co-transfected with Flag-hTERT and MKRN1-V5 were either untreated or treated for 2 hours with 10 µM MG132. Anti-Flag immunoprecipitates were analyzed by immunoblotting using an anti-V5 antibody probe. The left panel shows the immunoblot of cell lysates (3% of the precipitated lysates) probed with anti-V5 antibody. Flag-hTERT was visualized with an anti-Flag antibody probe.

Ubiquitination is carried out by a cascade of reactions catalyzed by ubiquitin-activating enzyme (E1), ubiquitin-conjugating enzyme (E2), and ubiquitin ligase (E3) (Hershko et al. 1998; Pickart et al. 2001). E3 proteins are known to play a pivotal role in determining the specificity of the system by recognizing target substrates. The inventors established a yeast two-hybrid system to search for an E3 ligase involved in hTERT degradation. With the C-terminal domain of hTERT as bait (residues 946-1132), the inventors identified proteins that interact with hTERT (FIG. 3A). One of the isolated clones contains a $C_3HC_4$-type RING finger domain that is present in many E3 ubiquitin ligases (Joazeiro et al. 1999; Levkowitz et al. 1999; Lorick et al. 1999). It was discovered that the protein was identical to the Makorin ring finger protein 1 (MKRN1) (Gray et al. 2000). MKRN1 is uniformly expressed in all tissues and encodes a putative ribonucleoprotein with a distinctive array of zinc-finger motifs, including four $C_3H$ zinc-finger motifs, an unusual Cys-His motif, and a highly conserved RING finger domain (FIG. 3B). MKRN1 orthologs have been identified in a wide spectrum of species (from invertebrates to vertebrates), suggesting an ancient origin of this highly conserved gene (Gray et al. 2000).

The physical interaction between MKRN1 and hTERT was examined by co-immunoprecipitation experiments in cells cotransfected with C-terminal HA-tagged hTERT and MKRN1-V5 expression vectors (FIG. 3C). The data show that MKRN1 was barely detectable in lysates directly probed with anti-V5 antibody (FIG. 3C, lanes 1 and 3). This suggests that MKRN1 may be rapidly degraded through auto-ubiquitination like other ring finger proteins that promote their own ubiquitination/degradation (Joazeiro and Weissman 2000). In the presence of ALLnN, however, there was a significant increase in both unmodified and ubiquitinated MKRN1 species (FIG. 3C, lanes 2 and 4). Immunoprecipitation of cell lysates with anti-HA antibody (hTERT) and subsequent immunoblot analysis with anti-V5 antibody (MKRN1) revealed that hTERT co-immunoprecipitated with MKRN1 in cells treated with ALLnN but not in negative drug control cells (FIG. 3C, compare lanes 7 and 8), suggesting that hTERT binds to MKRN1 in mammalian cells. When this experiment was modified using N-terminal Flag-tagged hTERT and MKRN1-V5 expression vectors with a different proteasome inhibitor (MG132), essentially identical results were obtained (FIG. 3D).

MKRN1 is an E3 Ubiquitin-Ligase that Enhances Ubiquitination of hTERT

Figure 4:
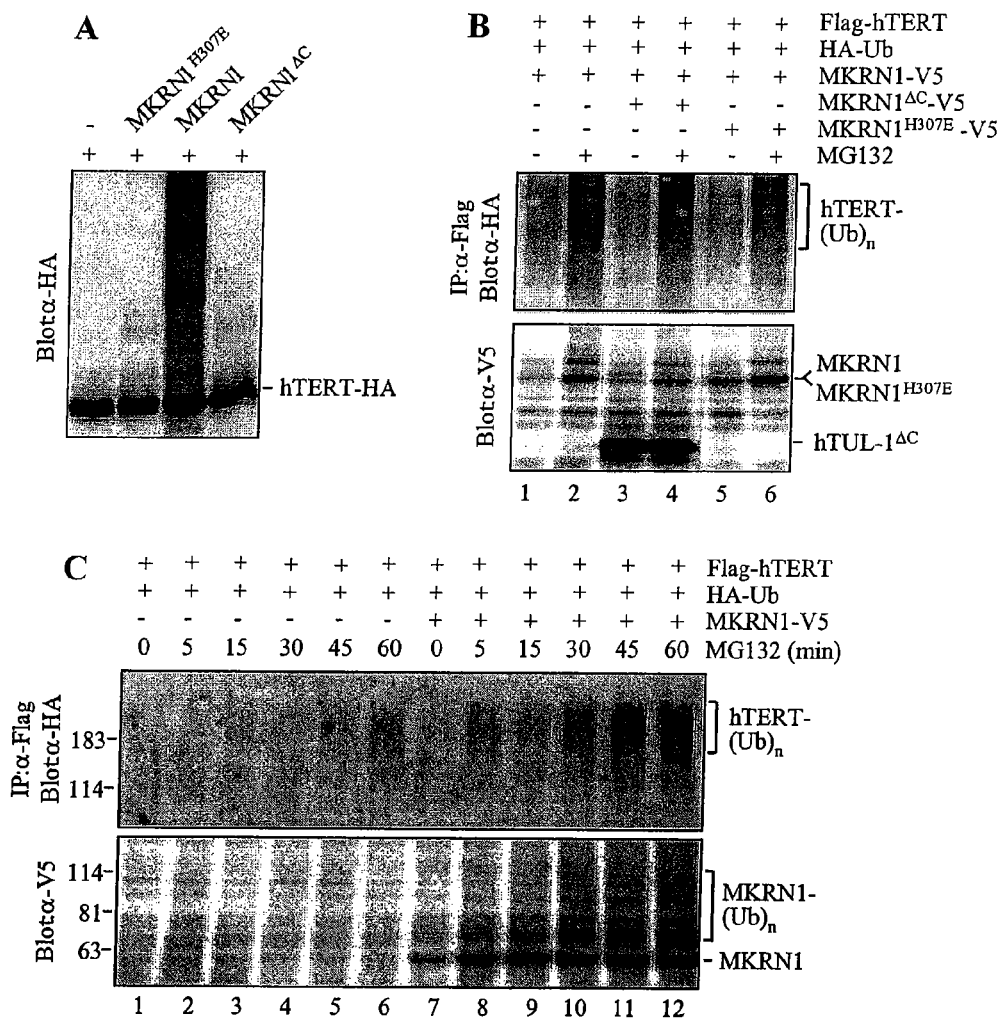
FIG. 4. MKRN1 functions as an E3 ubiquitin-ligase for hTERT in vitro and in vivo. (A) HA-tagged hTERT (residues 946-1132) was incubated MKRN1 or mutants in the presence of E1, E2, His$_6$-ubiquitin (6×His tag disclosed as SEQ ID NO: 7). Samples were resolved by 6% SDS-PAGE and analyzed by immunoblotting with an anti-HA antibody probe. (B) H1299 cells were co-transfected with Flag-hTERT, HA-ubiquitin, MKRN1-V5, and together with either MKRN1$^{H307E}$-V5 or MKRN1$^{\Delta c}$-V5 as specified. Cells were untreated or treated with 10 μM MG132 for 2 hours. Anti-Flag immunoprecipitates and cell lysates were analyzed by immunoblotting with anti-HA antibody and anti-V5 antibody probes, respectively. (C) H1299 cells co-transfected with Flag-hTERT and HA-ubiquitin, and together with or without MKRN1-V5 as indicated were treated with 10 μM MG132 for the indicated times. Anti-Flag immunoprecipitates and cell lysates were analyzed by immunoblotting with anti-HA antibody and anti-V5 antibody probes, respectively.

We next investigated the involvement of MKRN1 in ubiquitination of hTERT. In vitro ubiquitination assays using purified components showed that the C-terminal domain (residues 946-1132) of hTERT was efficiently ubiquitinated by wild-type MKRN1, but not by mutants MKRN1$^{H307E}$ or MKRN1$^{\Delta C}$ (FIG. 4A). Thus, while MKRN1 is an E3 ligase for hTERT, mutating the RING finger domain destroys this activity in vitro, indicating that the RING finger domain is indispensable for E3 activity.

To investigate whether MKRN1 contributes to the ubiquitination of hTERT in vivo, H1299 cells were cotransfected with Flag-hTERT, HA-ubiquitin, and MKRN1-V5 constructs, and immunoprecipitated with anti-Flag antibody followed by immunoblotting with anti-HA antibody. Ubiquitin conjugates of hTERT were easily detected in the presence of MG132 (FIG. 4B, lane 2 in upper blot). The amount of ubiquitinated hTERT was significantly reduced in cells cotransfected with MKRN1 plus MKRN1$^{H307E}$ (lane 6) compared to cells transfected with MKRN1 alone (lane 2) or in cells cotransfected with MKRN1 plus MKRN1$^{\Delta C}$ (lane 4). These data demonstrate that mutating the RING finger in MKRN1$^{H307E}$ does not impair its ability to interact with hTERT but disrupts the domain structure of the ubiquitin ligase activity, thereby yielding a dominant negative phenotype. When the levels of ectopically expressed MKRN1 and mutants were examined, MKRN1 expression was clearly elevated by MG132 treatment (FIG. 4B, compare lanes 1 and 2 in lower blot). In contrast, MG132 had no effect on the amount of MKRN1$^{\Delta C}$ (compare lanes 3 and 4), suggesting that the deleted C-terminal region is required for auto-ubiquitination of MKRN1. When both MKRN1 and MKRN1$^{H307E}$ were cotransfected, we were able to detect MKRN1$^{H307E}$ in the absence of MG132 although the expression level was slightly less (~2-fold) compared with that elicited by the MG132 treatment (compare lanes 5 and 6). Thus, mutating the histidine residue in the RING finger motif inhibits auto-ubiquitination.

To examine the in vivo role of MKRN1 in ubiquitination of hTERT, the inventors cotransfected H1299 cells with Flag-hTERT plus HA-ubiquitin and immunoprecipitated with anti-Flag antibody followed by immunoblotting with anti-HA antibody. Although no hTERT-ubiquitin conjugates were observed in untreated cells in this short exposed blot (FIG. 4C, lane 1 in upper blot), low levels were detected after 45-60 minutes of MG132 treatment (lanes 5 and 6). In marked contrast, co-expression of MKRN1 caused a dramatic increase in the amount of ubiquitinated hTERT species (lanes 7-12). When the expression levels of MKRN1 were examined by immunoblotting with anti-V5 antibody, both unmodified and polyubiquitinated MKRN1 species increased in a time-dependent manner in response to MG132 treatment (FIG. 4C, lanes 7-12 in lower blot). On the basis of these data, the inventors conclude that MKRN1 is an E3 ligase for hTERT ubiquitination in mammalian cells. Although our findings show that MKRN1 associates with and efficiently ubiquitinates hTERT, the foregoing data does not exclude the possibility of other E3 ligases for hTERT. The Hsp90/Hsp70- associated U-box ubiquitin ligase CHIP (carboxy terminus Hsc70-interacting protein) may mediate the GA-stimulated degradation of some Hsp90 client proteins (Connell et al. 2001; Meacham et al. 2001). Whether CHIP E3 activity regulates in vivo stability of hTERT remains to be elucidated.
Overexpression of MKRN1 Decreased Telomerase Activity and Telomere Length.

Figure 5:
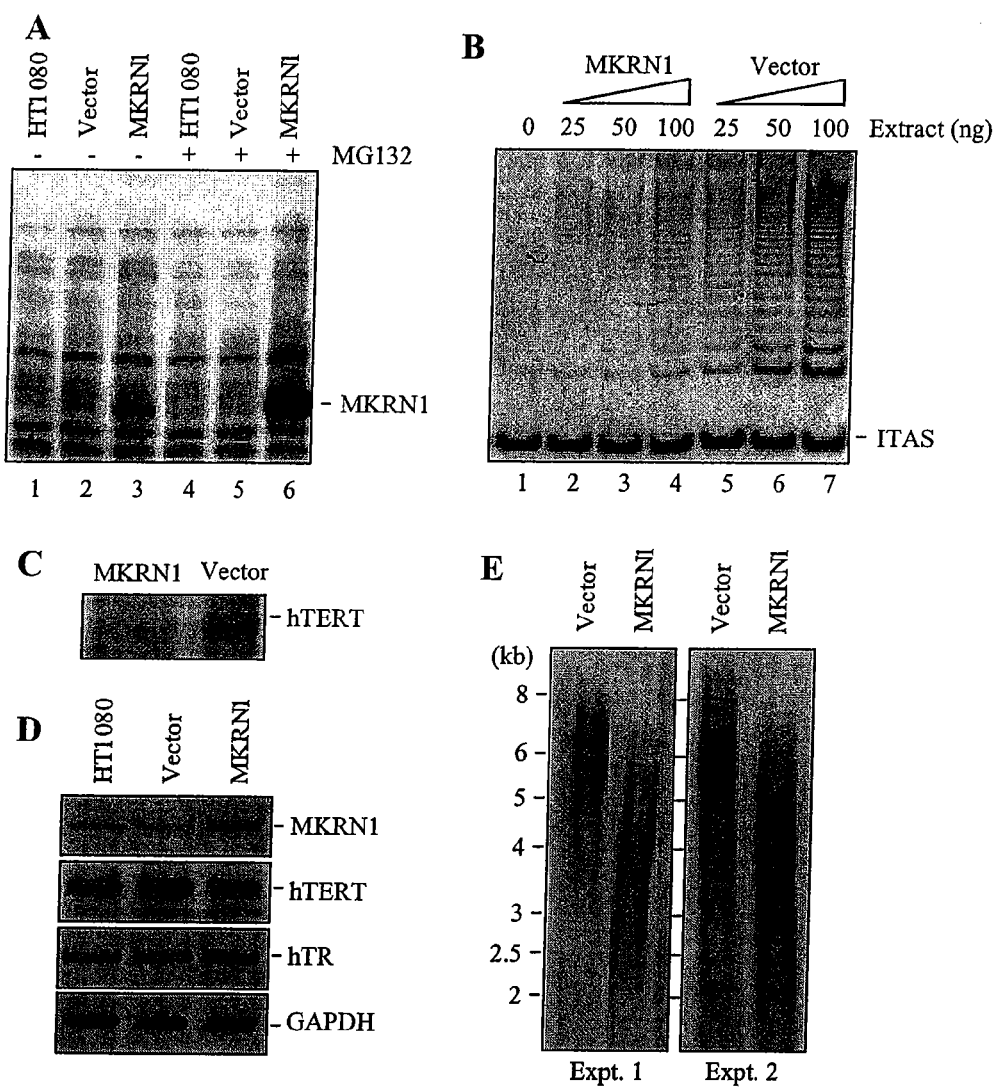
FIG. 5. Overexpression of MKRN1 decreases telomerase activity and telomere length. (A) HT1080 cells were stably transfected with MKRN1-V5 or an empty vector. The cells were untreated or treated for 2 hours with 10 μM MG132. Cell lysates were analyzed by immunoblotting with anti-V5 antibody probe. (B) Stable HT1080 cell lines (MKRN1 and vector) were harvested at 45 PD, and telomerase activities were measured with different amounts of proteins using the TRAP assay. The lane labeled LB corresponds to the negative control (lysis buffer only). ITAS represents the internal telomerase assay standard. (C) Cell lysates from stable HT1080 cell lines were analyzed by immunoprecipitation with anti-hTERT antibody followed by immunoblotting using same antibody probe. (D) Representative results of RT-PCR analysis for the expression of MKRN1, hTERT, and hTR in stable HT1080 cell lines. RT-PCR products from each sample were normalized to glyceraldehyde-3-phosphate dehydrogenase (GAPDH) signal. (E) Stable HT1080 cell lines were harvested at 45 PD, and genomic DNA was digested with RsaI and HinfI, followed by Southern blotting using a telomere repeat probe.

Because MKRN1 functions as an E3 ligase for hTERT ubiquitination in vivo, the inventors examined whether ectopic expression of MKRN1 affects telomerase activity. The inventors established HT1080 cell lines stably expressing MKRN1 (or an empty vector negative control). Levels of ectopically expressed MKRN1 were examined by immunoblotting with anti-V5 antibody (FIG. 5A). Treatment of MG132 resulted in a substantial increase in MKRN1 compared to untreated cells (compare lanes 3 and 6). Cells expressing MKRN1 and the empty vector grew normally and exhibited no detectable differences in growth rates or morphology over 45 population doublings (PD). After 45 PD, the inventors compared telomerase activity in stable cell lines expressing MKRN1 and the empty vector. Telomerase activity in cells expressing MKRN1 was decreased by ~5-fold relative to the control cell line (FIG. 5B). The overexpression of MKRN1 resulted in a down-regulation of the endogenous hTERT protein (FIG. 5C). These results suggest that MKRN1 acts as a negative regulator of telomerase. However, it is not clear whether this decrease is due to a MKRN1-related decrease in the expression of hTERT or hTR genes. To address this possibility, the impact of MKRN1 on gene expression of hTERT and hTR was evaluated using RT-PCR analysis (Kim et al. 2002). Whereas MKRN1 mRNA level was ~5-fold higher in cells expressing the gene (relative to control cells), we observed no significant differences in steady-state levels of hTERT mRNA or hTR transcripts in cell lines expressing MKRN1 and the empty vector (FIG. 5D). To examine whether MKRN1-mediated decrease in telomerase activity was attended by changes in telomere lengths, we performed a terminal restriction fragment (TRF) size analysis (Lee et al. 2004). Control cells exhibited an average telomere length of ~6 kb with most fragments spread over a range of approximately 5 to 7 kb (FIG. 5E). Telomeres were clearly shortened in the clones expressing MKRN1 with a decrease in TRF length to ~4 kb and spanning down to roughly 2.5 kb. These findings suggest that MKRN1 exerts a negative role in telomere length maintenance and/or regulation.

The data presented herein demonstrates that MKRN1 markedly enhances hTERT ubiquitination in the absence of GA treatment. This suggests that MKRN1 functions as an E3 ligase for the constitutive ubiquitination of mature hTERT assembled with hTR in the nucleus when the molecular chaperone Hsp90 is intact. Additionally, MKRN1 may perform this same function with newly synthesized hTERT in cytoplasm. Ubiquitination of hTERT may be regulated by changes in the expression and activity of MKRN1 and de-ubiquitinating enzymes. Moreover, continued expression of MKRN1 in telomerase-positive cells resulted in a decrease in telomerase activity and cells with shortened telomeres. Thus, MKRN1 regulates telomerase activity and telomere length through dynamic control of hTERT protein stability. The function of telomerase during development, aging, and cancer has been extensively studied (Kim et al. 2002). MKRN1, a post-translational modifier of hTERT, may play an important role in telomere length maintenance and/or regulation through ubiquitin-mediated proteolysis of hTERT.

Example 2

Identification of hMKRN1 Interactive Factors by Yeast Two-Hybrid Screening

Yeast two-hybrid screens similar to that described in Example 1 are implemented, except instead of screening with pLexA-hTERT, pLexA-MKRN1 with the same HeLa cDNA library fused to the activation domain vector pB42AD (Clonetech) is used. This will allow identification additional protein partners for MKRN1 E3 ubiquitin ligase.

Prior to setting up the system with MKRN as bait, autoactivation MKRN1 in yeast is checked, since it must be verified that DNA binding fusions with MKRN do not activate transcription alone. To ensure that the MKRN1-DNA binding fusion proteins are behaving correctly (eg., properly folded), a known positive couple (hTERT as prey and MKRN1 as bait) is verified. The inventors showed that $hTERT^{946-1132}$ gave a strong positive LacZ signal with WT hMKRN1 prey; therefore, reversing the partners will give concordant results if the MKRN1 is a functional partner. In fact, for any subsequent positives obtained by 2-hybrid screening described below, we will perform a reciprocal swap like this to ensure concordance. Note also that screening with libraries selects for optimized interactions. It is known, for example that subdomains may interact better than whole proteins (probably reflects domain folding, stearic access and so forth). For this reason, our original screening using hTERT as bait (FIG. 3) was successful with a domain spanning residues 946-1132 of hTERT. It is reasonable to propose a similar approach using MKRN1 as bait. The 482 amino acid hMKRN1 are divided into subclone domains in the pLexA-MKRN1 bait. Positive and negative controls (hTERT and TRF1 respectively) are used. As shown in xx FIG. 12, we will prepare a series of intact as well as overlapping and non-overlapping clones. The domain organization of hMKRN1 is useful in selecting the appropriate clones. For example, domain analysis by "NCBI Conserved Domain Search" algorithm reveals that $hMKRN1^{132-240}$ contains a strong homology to RecQ helicase. Given the conservation of MKRN1 (Reprint #1), it may have other activities and targets that are unrelated to the ubiquitin-proteasome pathway. Moreover, the RecQ domain should not be affected by a single residue change in the RING finger at H307; thus the $hMKRN1^{H307E}$ mutant should be able to bind these targets in the absence of E3 ubiquitin ligase function. All of these constructs may be subcloned, sequenced and checked for their ability to couple with $hTERT^{946-1132}$ using the 2-hybrid assay. These data enable sorting out other positives since the regions of binding between hTERT/MKRN are established; thus, any new genes found to interact with non-hTERT binding sites signify a novel partner proteins (for example binding partners in RecQ helicase).

Characterization of Specificity

Positives are characterized similar to the strategies described in Example 1. Depending on the number of positives, different approaches are taken. For example, a limited number of positives are obtained involving only a few of our bait constructs, a new transformation with positive and negative controls (including empty vectors) is repeated and re-assayed for specificity, bait swaps and then sequenced. If a larger number of positives (50-100) are obtained, direct sequence analysis is conducted. Blast search characterizations for known proteins, conserved domains and homology with existing genes and gene products, are conducted see Example 1. Sequence data may be analyzed. For example, genes not in frame with the activation domain, indications of gene inversions (polyAAA tail position), genes encoding RNA or retroposons would be less interesting.

Positive interactions is also confirmed outside the yeast system. In brief, pull downs and Co-IP experiments in a model cell system (such as HeLa cells which express low levels of MKRN1 and HEK293 cells expressing high levels of MKRN1) are performed. Co-localization using immunofluorescence and confocal microscopy to validate the 2-hybrid couple in mammalian cells may also be performed.

RELEVANT REFERENCES

Artandi, S. E., Alson, S., Tietze, M. K., Sharpless, N. E., Ye, S., Greenberg, R. A., Castrillon, D. H., Homer, J. W., Weiler, S. R., Carrasco, R. D., and DePinho, R. A. 2002. Constitutive telomerase expression promotes mammary carcinomas in aging mice. *Proc. Natl. Acad. Sci. USA* 99: 8191-8196.

Blackburn, E. H. 1991. Structure and function of telomeres. *Nature* 350: 569-573.

Blackburn, E. H. 1992. Telomerases. *Annu. Rev. Biochem.* 61: 113-129.

Blasco, M. A., Lee, H. W., Hande, M. P., Samper, E., Lansdorp, P. M., DePinho, R. A., and Greider, C. W. 1997. Telomere shortening and tumor formation by mouse cells lacking telomerase RNA. *Cell* 91: 25-34.

Bodnar, A. G., Ouellette, M., Frolkis, M., Holt, S. E., Chiu, C. P., Morin, G B., Harley, C. B., Shay, J. W., Lichtsteiner, S., and Wright, W. E. 1998. Extension of life-span by introduction of telomerase into normal human cells. *Science* 279: 349-352.

Citri, A., Alroy, I., Lavi, S., Rubin, C., Xu, W., Grammatikakis, N., Patterson, C., Neckers, L., Fry, D. W., and Yarden, Y. 2002. Drug-induced ubiquitylation and degradation of ErbB receptor tyrosine kinases: implications for cancer therapy. *EMBO J.* 21: 2407-2417.

Connell, P., Ballinger, C. A., Jiang, J., Wu, Y, Thompson, L. J., Hohfeld, J., and Patterson, C. 2001. The co-chaperone CHIP regulates protein triage decisions mediated by heat-shock proteins. *Nat. Cell Biol.* 3: 93-96.

Counter, C. M., Avilion, A. A., LeFeuvre, C. E., Stewart, N. G., Greider, C. W., Harley, C. B., and Bacchetti, S. 1992. Telomere shortening associated with chromosome instability is arrested in immortal cells which express telomerase activity. *EMBO J.* 11: 1921-1929.

Forsythe H. L., Jarvis, J. L., Turner, J. W., Elmore, L. W., and Holt, S. E. 2001. Stable association of hsp90 and p23, but Not hsp70, with active human telomerase. *J. Biol. Chem.* 276: 15571-15574.

Girnita, L., Girnita, A., and Larsson, O. 2003. Mdm2-dependent ubiquitination and degradation of the insulin-like growth factor 1 receptor. *Proc. Natl. Acad. Sci. USA* 100: 8247-8252.

Goetz, M. P., Toft, D. O., Ames, M. M., and Erlichman, C. 2003. The Hsp90 chaperone complex as a novel target for cancer therapy. *Ann. Oncol.* 14: 1169-1176.

Gray, T. A., Hernandez, L., Carey, A. H., Schaldach, M. A., Smithwick, M. J., Rus, K., Marshall Graves, J. A., Stewart, C. L., and Nicholls, R. D. 2000. The ancient source of a distinct gene family encoding proteins featuring RING and C(3)H zinc-finger motifs with abundant expression in developing brain and nervous system. *Genomics* 66: 76-86.

Greider, C. W. 1996. Telomere length regulation. *Annu. Rev. Biochem.* 65: 337-365.

Harley, C. B. 1991. Telomere loss: mitotic clock or genetic time bomb? *Mutat. Res.* 256: 271-282.

Hershko, A., and Ciechanover, A. 1998. The ubiquitin system. *Annu. Rev. Biochem.* 67: 425-479.

Holt, S. E., Aisner, D. L., Baur, J., Tesmer, V. M., Dy, M., Ouellette, M., Trager, J. B., Morin, G. B., Toft, D. O., Shay, J. W., Wright, W. E., and White, M. A. 1999. Functional requirement of p23 and Hsp90 in telomerase complexes. *Genes Dev.* 13: 817-826.

Isaacs, J. S., Jung, Y J., Mimnaugh, E. G., Martinez, A., Cuttitta, F., and Neckers, L. M. 2002. Hsp90 regulates a von Hippel Lindau-independent hypoxia-inducible factor-1 alpha-degradative pathway. *J. Biol. Chem.* 277: 29936-29944.

Joazeiro, C. A., Wing, S. S., Huang, H., Leverson, J. D., Hunter, T., and Liu, Y. C. 1999. The tyrosine kinase negative regulator c-Cbl as a RING-type, E2-dependent ubiquitin-protein ligase. *Science* 286: 309-312.

Kim, J. H., Lee, G. E., Kim, J. C., Lee, J. H., and Chung, I. K. 2002. A novel telomere elongation in an adriamycin-resistant stomach cancer cell line with decreased telomerase activity. *Mol. Cells* 13: 228-236.

Kim, J. H., Kim, J. H., Lee, G E., Lee, J. E., and Chung, I. K. 2003. Potent inhibition of human telomerase by nitrostyrene derivatives. *Mol. Pharmacol.* 63: 1117-11124.

Kim, N. W., Piatyszek, M. A., Prowse, K. R., Harley, C. B., West, M. D., Ho, P. L. C., Coviello, G M., Wright, W. E., Weinrich, S. L., and Shay, J. W. 1994. Specific association of human telomerase activity with immortal cells and cancer. *Science* 266: 2011-2015.

Kim, N. W., and Wu, F. 1997. Advances in quantification and characterization of telomerase activity by the telomeric repeat amplification protocol (TRAP). *Nucleic Acids Res.* 25: 2595-2597.

Kim, S. H., Kaminker, P., and Campisi, J. 2002. Telomeres, aging and cancer: in search of a happy ending. *Oncogene* 21: 503-511.

Joazeiro, C. A., and Weissman, A. M. 2000. RING finger proteins: mediators of ubiquitin ligase activity. *Cell* 102: 549-552.

Lee, G E., Yu, E. Y., Cho, C. H., Lee, J., Muller, M. T., and Chung, I. K. 2004. DNA-protein kinase catalytic subunit-interacting protein KIP binds telomerase by interacting with human telomerase reverse transcriptase. *J. Biol. Chem.* 289: 34750-34755.

Levkowitz, G., Waterman, H., Ettenberg, S. A., Katz, M., Tsygankov, A. Y., Alroy, I., Lavi, S., Iwai, K., Reiss, Y., Ciechanover, A., Lipkowitz, S., and Yarden, Y. 1999. Ubiquitin ligase activity and tyrosine phosphorylation underlie suppression of growth factor signaling by c-Cbl/Sli-1. *Mol. Cell* 4: 1029-1040.

Lingner, J., Cooper, J. P., and Cech, T. R. 1995. Telomerase and DNA end replication: no longer a lagging strand problem? *Science* 269: 1533-1534.

Liu, J. P. 1999. Studies of the molecular mechanisms in the regulation of telomerase activity. *FASEB J.* 13: 2019-2104.

Lorick, K. L., Jensen, J. P., Fang, S., Ong, A. M., Hatakeyama, S., and Weissman, A. M. 1999. RING fingers mediate ubiquitin-conjugating enzyme (E2)-dependent ubiquitination. *Proc. Natl. Acad. Sci. USA* 96:11364-11369.

Meacham, G. C., Patterson, C., Zhang, W., Younger, J. M., and Cyr, D. M. 2001. The Hsc70 co-chaperone CHIP targets immature CFTR for proteasomal degradation. *Nat. Cell Biol.* 3: 100-105.

Meyerson, M., Counter, C. M., Eaton, E. N., Ellisen, L. W., Steiner, P., Caddle, S. D., Ziaugra, L., Beijerbergen, R. L., Davidoff, M. J., Liu, Q., Bacchetti, S., Haber, D. A., and Weinberg, R. A. 1997. hEST2, the putative human telomerase catalytic subunit gene, is up-regulated in tumor cells and during immortalization. *Cell* 90: 785-795.

Nakamura, T. M., and Cech, T. R. 1998. Reversing time: origin of telomerase. *Cell* 92: 587-590.

Park, S. M., Yoon, J. B., and Lee, T. H. 2004. Receptor interacting protein is ubiquitinated by cellular inhibitor of apoptosis proteins (c-IAP1 and c-IAP2) in vitro. *FEBS Lett.* 566: 151-156.

Pickart, C. M. 2001. Mechanisms underlying ubiquitination. *Annu. Rev. Biochem.* 70: 503-533.

Seimiya, H., Sawada, H., Muramatsu, Y., Shimizu, M., Ohko, K., Yamane, K., and Tsuruo, T. 2000. Involvement of 14-3-3 proteins in nuclear localization of telomerase. *EMBO J.* 19: 2652-2661.

Wang, J., Xie, L. Y., Allan, S., Beach, D., and Hannon, G. J. 1998. Myc activates telomerase. *Genes Dev.* 12: 1769-1774.

Wu, K.-J., Grandori, C., Amacker, M., Simon-Vermot, N., Polack, A., Lingner, J., and Dalla-Favera, R. 1999. Direct activation of TERT transcription by c-MYC. *Nature Genet.* 21: 220-224.

Zhou, X. Z., and Lu, K. P. 2001. The Pin2/TRF1-interacting protein PinX1 is a potent telomerase inhibitor. *Cell* 107: 347-359.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A method for isolating and identifying a potential candidate for affecting activity of telomerase in telomerase positive cancer cells; said method comprising
   (i) applying a yeast-two-hybrid procedure in which a bait vector carries a polynucleotide sequence encoding a bait MKRN polypeptide, wherein said MKRN polypeptide comprises SEQ ID NO. 2, and a prey vector carries a sequence from a cDNA or genomic DNA library encoding a prey polypeptide;
   (ii) transforming yeast host cells with said first and second hybrid vectors;
   (iii) isolating positive transformed cells;
   (iv) extracting second hybrid vector from said positive transformed cells to obtain a sequence encoding an interacting protein which binds to said MKRN polypeptide expressed by said first hybrid vector; and
   (v) identifying a potential candidate for affecting activity of telomerase in telomerase positive cancer cells by further identifying from the interacting polypeptide obtained from step (iv) the polypeptide that modulates the expression or activity of said MKRN polypeptide;
   whereby the identified polypeptide that modulates the expression or activity of said MKRN polypeptide is the potential candidate for affecting activity of telomerase in telomerase positive cancer cells.

* * * * *

SEQUENCE LISTING

```
<160> NUMBER OF SEQ ID NOS: 7

<210> SEQ ID NO 1
<211> LENGTH: 3025
<212> TYPE: DNA
<213> ORGANISM: Homo sapiens

<400> SEQUENCE: 1
gaacgggtgc ctcagtgtcc ttccctccc ctcgcctggc ctcgcgtcct ctccccgcag      60
ccggaccgga actatgtgat cccggaagtt ccgggccttt gctgtgtggg ataaacagta    120
atggcggagg ctgcaactcc cggaacaaca gccacaacat caggagcagg agcggcagcg    180
gcgacggcgg cagcagcctc ccccaccccg atccccacag tcaccgcccc gtccctgggg    240
gcgggcggag ggggcggcgg cagcgacggc agcggcggcg gctggactaa acaggtcacc    300
tgcaggtatt ttatgcatgg ggtttgtaag gaaggagaca actgtcgcta ctcgcatgac    360
ctctctgaca gtccgtatag tgtagtgtgc aagtattttc agcgagggta ctgtatttat    420
ggagaccgct gcagatatga acatagcaaa ccattgaaac aggaagaagc aactgctaca    480
gagctaacta caaagtcatc ccttgctgct tcctcaagtc tctcatcgat agttggacca    540
cttgttgaaa tgaatacagg cgaagctgag tcaagaaatt caaactttgc aactgtagga    600
gcaggttcag aggactgggt gaatgctatt gagtttgttc ctgggcaacc ctactgtggc    660
cgtactgcgc cttcctgcac tgaagcaccc ctgcagggct cagtgaccaa ggaagaatca    720
gagaaagagc aaaccgccgt ggagacaaag aagcagctgt gcccctatgc tgcagtggga    780
gagtgccgat acggggagaa ctgtgtgtat ctccacggag attcttgtga catgtgtggg    840
ctgcagctcc tgcatccaat ggatgctgcc cagagatcgc agcatatcaa atcgtgcatt    900
gaggcccatg agaaggacat ggagctctca tttgccgtgc agcgcagcaa ggacatggtg    960
tgtgggatct gcatggaggt ggtctatgag aaagccaacc ccagtgagcg ccgcttcggg   1020
atcctctcca actgcaacca cacctactgt ctcaagtgca ttcgcaagtg gaggagtgct   1080
aagcaatttg agagcaagat cataaagtcc tgcccagaat gccggatcac atctaacttt   1140
gtcattccaa gtgagtactg ggtggaggag aaagaagaga gcagaaact cattctgaaa   1200 tacaaggagg caatgagcaa caaggcgtgc aggtattttg atgaaggacg tgggagctgc   1260
```

```
ccatttggag ggaactgttt ttacaagcat gcgtaccctg atgccggtag agaggagcca    1320
cagagacaga aagtgggaac atcaagcaga taccgggccc aacgaaggaa ccacttctgg    1380
gaactcattg aggaaagaga aacagcaac  cccctttgaca acgatgaaga agaggttgtc   1440
acctttgagc tgggcgagat gttgcttatg cttttggctg caggtgggga cgacgaacta    1500
acagactctg aagatgagtg ggacttgttt catgatgagc tggaagattt ttatgacttg    1560
gatctatagc aaccttgcgt ggcgtgtgaa ctggtctgct gacctcagac agcagctgtc    1620
ccctgtggtg gtgtggcagt cctgttgttc tctcctaggc aggcctctca actccaggtg    1680
ctgtcctaag aattttttacc cagggcctgt cttctcaacc cctcacccttt ccctgaggag   1740
tgtgttgttt ccctgttga aaaaagttac aaaaataaat cttaaagtta gttttttgta     1800
acacgaattt aactgtcaga cagttagtgt aagtgtgttg cgtcatctgt tttcaaccag    1860
attgcattta tggactttttc acacactcat tttgaggacc ccaggttcaa aagtaaaagc   1920
actggccctg cttttggggtc caagaatagg agtgatgggt gaagggacct aacctggcca   1980
atagccctct gccccacaca tgggatgtgg atccttgacg tttctggtga atctgcaca    2040
tctgtgttt  tatatctgtt ccctaccctg taatccctac cacgtgcact tgttctgtgg    2100
ttttggtctc ttgtttaatt gcacacaagt aatactactg ggtaaccaga atcaggtgtg    2160
aatgtgttga gatttttttac tgttttgcat gataggaaaa ttgaaaaaga atacgtataa    2220
aagatagaga ggcataacat caatgcagag ttggaagttg gctcccaagg gctgacatgg    2280
tgtgagtgtg tgggtgtgtg ataagcttct catccctgca tagatgcagt attcttagcc    2340
ttagtagaaa aacctggttt agtggtttaa gccttgtgtg gcaaatagat cttaaagggc    2400
aaagcagtat attggtagtt gtcaatatag cagtgctagc tctgtctata taaatagaga    2460
aatgggggtta gccatagagg ttaaaactac ctggttatcc catataataa cacaaactgg   2520
gtcttggata cacagttgta tttaatgttt tacgatctac cctttccagt acaggcactt    2580
tctgagaaac ctttgtcctc acttgaggca ttttgttgtc gggttttttgt gtttgttttt   2640
gtgggtattt gcctcattcc accccctgagc tttcaggtag acagacgtga ttcaaaactc   2700
tgttctaagg tgtttattgt agtggagtaa tgggtttgca gtgataagtc atactttttcc   2760
accgaaaggg agggcttggg aatccctgag attagctaaa gttaagttgt tggagaattc    2820
cttgattgga aattgtacct ttgtgttttg ttgctctgtt tcctgaaaat aactcgggga    2880
tgctcctggt ttgtccatct actgctttga ttccttggat cccacccatt ctttcacttt    2940
aagaaaaaac aaataattgt tgcagaggtc tctgtatttt gcagctgccc ttttgtaaga    3000
agcactttttc ccaaataaaa caatt                                          3025
```

<210> SEQ ID NO 2
<211> LENGTH: 482
<212> TYPE: PRT
<213> ORGANISM: Homo sapiens

<400> SEQUENCE: 2

```
Met Ala Glu Ala Ala Thr Pro Gly Thr Thr Ala Thr Thr Ser Gly Ala
  1               5                  10                  15

Gly Ala Ala Ala Ala Thr Ala Ala Ala Ala Ser Pro Thr Pro Ile Pro
             20                  25                  30

Thr Val Thr Ala Pro Ser Leu Gly Ala Gly Gly Gly Gly Gly Gly Ser
         35                  40                  45

Asp Gly Ser Gly Gly Gly Trp Thr Lys Gln Val Thr Cys Arg Tyr Phe
     50                  55                  60
```

```
Met His Gly Val Cys Lys Glu Gly Asp Asn Cys Arg Tyr Ser His Asp
 65                  70                  75                  80
Leu Ser Asp Ser Pro Tyr Ser Val Val Cys Lys Tyr Phe Gln Arg Gly
                 85                  90                  95
Tyr Cys Ile Tyr Gly Asp Arg Cys Arg Tyr Glu His Ser Lys Pro Leu
            100                 105                 110
Lys Gln Glu Glu Ala Thr Ala Thr Glu Leu Thr Thr Lys Ser Ser Leu
        115                 120                 125
Ala Ala Ser Ser Ser Leu Ser Ser Ile Val Gly Pro Leu Val Glu Met
    130                 135                 140
Asn Thr Gly Glu Ala Glu Ser Arg Asn Ser Asn Phe Ala Thr Val Gly
145                 150                 155                 160
Ala Gly Ser Glu Asp Trp Val Asn Ala Ile Glu Phe Val Pro Gly Gln
            165                 170                 175
Pro Tyr Cys Gly Arg Thr Ala Pro Ser Cys Thr Glu Ala Pro Leu Gln
            180                 185                 190
Gly Ser Val Thr Lys Glu Glu Ser Glu Lys Glu Gln Thr Ala Val Glu
        195                 200                 205
Thr Lys Lys Gln Leu Cys Pro Tyr Ala Ala Val Gly Glu Cys Arg Tyr
    210                 215                 220
Gly Glu Asn Cys Val Tyr Leu His Gly Asp Ser Cys Asp Met Cys Gly
225                 230                 235                 240
Leu Gln Leu Leu His Pro Met Asp Ala Ala Gln Arg Ser Gln His Ile
            245                 250                 255
Lys Ser Cys Ile Glu Ala His Glu Lys Asp Met Glu Leu Ser Phe Ala
            260                 265                 270
Val Gln Arg Ser Lys Asp Met Val Cys Gly Ile Cys Met Glu Val Val
        275                 280                 285
Tyr Glu Lys Ala Asn Pro Ser Glu Arg Arg Phe Gly Ile Leu Ser Asn
    290                 295                 300
Cys Asn His Thr Tyr Cys Leu Lys Cys Ile Arg Lys Trp Arg Ser Ala
305                 310                 315                 320
Lys Gln Phe Glu Ser Lys Ile Ile Lys Ser Cys Pro Glu Cys Arg Ile
            325                 330                 335
Thr Ser Asn Phe Val Ile Pro Ser Glu Tyr Trp Val Glu Glu Lys Glu
            340                 345                 350
Glu Lys Gln Lys Leu Ile Leu Lys Tyr Lys Glu Ala Met Ser Asn Lys
        355                 360                 365
Ala Cys Arg Tyr Phe Asp Glu Gly Arg Gly Ser Cys Pro Phe Gly Gly
    370                 375                 380
Asn Cys Phe Tyr Lys His Ala Tyr Pro Asp Ala Gly Arg Glu Glu Pro
385                 390                 395                 400
Gln Arg Gln Lys Val Gly Thr Ser Ser Arg Tyr Arg Ala Gln Arg Arg
            405                 410                 415
Asn His Phe Trp Glu Leu Ile Glu Glu Arg Glu Asn Ser Asn Pro Phe
            420                 425                 430
Asp Asn Asp Glu Glu Glu Val Val Thr Phe Glu Leu Gly Glu Met Leu
        435                 440                 445
Leu Met Leu Leu Ala Ala Gly Gly Asp Asp Glu Leu Thr Asp Ser Glu
    450                 455                 460
Asp Glu Trp Asp Leu Phe His Asp Glu Leu Glu Asp Phe Tyr Asp Leu
465                 470                 475                 480

Asp Leu
```

```
<210> SEQ ID NO 3
<211> LENGTH: 54
<212> TYPE: PRT
<213> ORGANISM: Homo sapiens

<400> SEQUENCE: 3

Cys Gly Ile Cys Met Glu Val Val Tyr Glu Lys Ala Asn Pro Ser Glu
 1               5                  10                  15

Arg Arg Phe Gly Ile Leu Ser Asn Cys Asn His Thr Tyr Cys Leu Lys
            20                  25                  30

Cys Ile Arg Lys Trp Arg Ser Ala Lys Gln Phe Glu Ser Lys Ile Ile
        35                  40                  45

Lys Ser Cys Pro Glu Cys
    50

<210> SEQ ID NO 4
<211> LENGTH: 54
<212> TYPE: PRT
<213> ORGANISM: Homo sapiens

<400> SEQUENCE: 4

Cys Gly Ile Cys Met Glu Val Val Tyr Glu Lys Ala Asn Pro Ser Glu
 1               5                  10                  15

Arg Arg Phe Gly Ile Leu Ser Asn Cys Asn Glu Thr Tyr Cys Leu Lys
            20                  25                  30

Cys Ile Arg Lys Trp Arg Ser Ala Lys Gln Phe Glu Ser Lys Ile Ile
        35                  40                  45

Lys Ser Cys Pro Glu Cys
    50

<210> SEQ ID NO 5
<211> LENGTH: 20
<212> TYPE: PRT
<213> ORGANISM: Homo sapiens

<400> SEQUENCE: 5

Cys Gly Ile Cys Met Glu Val Val Tyr Glu Lys Ala Asn Pro Ser Glu
 1               5                  10                  15

Arg Arg Phe Gly
            20

<210> SEQ ID NO 6
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ttagggttag ggttagggtt agggttaggg ttagggttag ggttagggtt agggttaggg      60
ttagggttag ggttagggtt agggttaggg ttagggttag ggttagggtt agggttaggg     120

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 7

His His His His His His
  1               5
```